US009980471B2

(12) United States Patent
Sachs et al.

(10) Patent No.: US 9,980,471 B2
(45) Date of Patent: May 29, 2018

(54) MINIATURE SWINE TRANSGENIC FOR ONE OR MORE COAGULATION FACTORS (71) Applicant: The General Hospital Corporation, Boston, MA (US)

(72) Inventors: David H. Sachs, Newton, MA (US); Martin Hertl, Gloucester, MA (US)

(73) Assignee: The General Hospital Corporation, Boston, MA (US)

( * ) Notice: Subject to any disclaimer, the term of this patent is extended or adjusted under 35 U.S.C. 154(b) by 469 days.

(21) Appl. No.: 14/403,764

(22) PCT Filed: Jun. 11, 2013

(86) PCT No.: PCT/US2013/045108
§ 371 (c)(1),
(2) Date: Nov. 25, 2014

(87) PCT Pub. No.: WO2013/188358
PCT Pub. Date: Dec. 19, 2013

(65) Prior Publication Data
US 2015/0106962 A1 Apr. 16, 2015

Related U.S. Application Data (60) Provisional application No. 61/672,049, filed on Jul. 16, 2012, provisional application No. 61/658,674, filed on Jun. 12, 2012.

(51) Int. Cl.
| *C12N 15/85* | (2006.01) |
| *C12N 5/071* | (2010.01) |
| *A01K 67/027* | (2006.01) |
| *C12N 9/10* | (2006.01) |
| *C12N 9/64* | (2006.01) |
| *C07K 14/745* | (2006.01) |

(52) U.S. Cl.
CPC ........ *A01K 67/0278* (2013.01); *C07K 14/745* (2013.01); *C12N 5/067* (2013.01); *C12N 9/1048* (2013.01); *C12N 9/6424* (2013.01); *C12N 9/6432* (2013.01); *C12N 9/6437* (2013.01); *C12N 9/6451* (2013.01); *C12N 15/8509* (2013.01); *A01K 2217/072* (2013.01); *A01K 2217/075* (2013.01); *A01K 2217/203* (2013.01); *A01K 2227/108* (2013.01); *A01K 2267/025* (2013.01)

(58) Field of Classification Search
CPC .......... A01K 67/0278; A01K 2217/072; A01K 2217/075; A01K 2217/203; A01K 2227/108; A01K 2267/025; C07K 14/745; C12N 5/067; C12N 9/1048; C12N 9/6424; C12N 9/6437; C12N 9/6451; C12N 15/8509
See application file for complete search history.

(56) References Cited

U.S. PATENT DOCUMENTS

| 5,614,187 A | 3/1997 | Sachs |
| 5,843,425 A | 12/1998 | Sachs et al. |
| 6,030,833 A | 2/2000 | Seebach et al. |
| 6,153,428 A | 11/2000 | Gustafsson et al. |
| 6,306,651 B1 | 10/2001 | Sachs |
| 6,344,596 B1 * | 2/2002 | Velander ............ A01K 67/0275 435/325 |
| 6,413,769 B1 | 7/2002 | Gustafsson et al. |
| 6,469,229 B1 | 10/2002 | Sachs et al. |
| 6,558,663 B1 | 5/2003 | Seebach et al. |
| 7,141,716 B2 | 11/2006 | Sachs et al. |
| 7,547,816 B2 | 6/2009 | Day et al. |
| 2003/0014770 A1 | 1/2003 | Gustafsson et al. |
| 2005/0266561 A1 * | 12/2005 | Wells ................. A01K 67/0275 435/455 |
| 2006/0128020 A1 | 6/2006 | Calos |
| 2009/0235369 A1 * | 9/2009 | Sasgary ............. A01K 67/0275 800/3 |
| 2013/0111614 A1 | 5/2013 | McGregor et al. |

FOREIGN PATENT DOCUMENTS

| RU | 2335537 | 10/2008 |
| WO | WO 1995/028412 | 10/1995 |
| WO | 2012/057527 | 3/2012 |

OTHER PUBLICATIONS

Lindsay et al., J. of Chromatography A, 1026: 149-157, 2004.*
Phelps et al., Science,299: 411-414, 2003.*
International Search Report and Written Opinion dated Oct. 2, 2013, 7 pgs.
Lee et al., Production of Recombinant Human Von Willebrand Factor in the Milk of Transgenic Pigs, Journal of Reproduction and Development 55(5): 484-490 (2009).
International Preliminary Report on Patentability in International Application No. PCT/US2013/045108, dated Dec. 16, 2014, 6 pages.
Burlak et al., "The fate of human platelets perfused through the pig liver: implications for xenotransplantation," Xenotransplantation, 17(5):350-61 (Sep.-Oct. 2010).
Chen et al., "Characterization of porcine factor VII, X and comparison with human factor VII, X," Blood Cells Mol Dis., 43(1):111-118 (Jul.-Aug. 2009).
Ekser et al., "Impact of thrombocytopenia on survival of baboons with genetically modified pig liver transplants: clinical relevance," Am. J. Transplant, 10:273-285 (Feb. 2010).
Fujioka et al., "Differential patterns of reaction of human natural antibodies to pig hepatocytes and vascular endothelium," Liver Transpl Surg., 1(2):85-93 (Mar. 1995).
Giles et al., "Clinical heterotransplantation of the liver," Transplant Proc., 2(4):506-12 (Dec. 1970) (Author Manuscript).
Gossler et al., "Transgenesis by means of blastocyst-derived embryonic stem cell lines," Proc. Natl. Acad. Sci. USA, 83:9065-9069 (Dec. 1986).
Joyner et al., "Production of a mutation in mouse En-2 gene by homologous recombination in embryonic stem cells," Nature, 338:153-6 (Mar. 1989).
Kim et al., "Up to 9-day survival and control of thrombocytopenia following α1,3-galactosyl transferase knockout swine liver xenotransplantation in baboons," Xenotransplantation, 19:256-64 (Jul.-Aug. 2012) (Author Manuscript).

(Continued)

*Primary Examiner* — Thaian N Ton
(74) *Attorney, Agent, or Firm* — Fish & Richardson P.C.

(57) ABSTRACT

Transgenic swine that express human coagulation factors, e.g., human coagulation factor VII, and/or one or more of human coagulation factors II, X and XII, and do not express the corresponding porcine coagulation factor or factors, as well as cells, tissues and organs derived therefrom, and their use in transplantation procedures.

14 Claims, 4 Drawing Sheets

(56) References Cited

OTHER PUBLICATIONS

Klymiuk et al., "Genetic modification of pigs as organ donors for xenotransplantation," Mol Reprod Dev., 77:209-221 (Mar. 2010).
Kolber-Simonds et al., "Production of α-1,3-galactosyltransferase null pigs by means of nuclear transfer with fibroblasts bearing loss of heterozygosity mutations," Proc. Natl. Acad. Sci. U. S. A, 101(19):7335-7340 (May 2004).
Koster and Schirmer, "Re-evaluation of the role of antifibrinolytic therapy with lysine analogs during cardiac surgery in the post aprotinin era," Curr Opin Anaesthesiol., 24(1):92-7 (Feb. 2011).
Kuwaki et al., "Heart transplantation in baboons using α1,3-galactosyltransferase gene-knockout pigs as donors: initial experience." Nat. Med., 11(1):29-31 (Jan. 2005).
Makowka and Cramer, "The pathogenesis of xenograft rejection," Clin Transplant., 8(2 Pt 2):145-54 (Apr. 1994).
Makowka et al., "Immunohistopathologic , lesions associated with the rejection of a pig-to-human liver xenograft," Transplant Proc., 26(3):1074-5 (Jun. 1994).
Makowka et al., "The use of a pig liver xenograft for temporary support of a patient with fulminant hepatic failure," Transplantation, 59(12):1654-9 (Jun. 27, 1995).
Mezrich et al., "Histocompatible miniature swine: an inbred large-animal model," Transplantation, 75(6):904-907 (Mar. 27, 2003).
Ozato et al., "Monoclonal antibodies to mouse major histocompatibility complex antigens," Transplantation, 34:113-120 (Sep. 1982).
Palmiter et al., "Germ-line transformation of mice," Ann. Rev. Genet., 20:465-99 (1986).
Powelson et al., "Porcine to primate orthotopic liver transplantation," Transplant Proc., 26:1353-1354 (Jun. 1994).
Prather et al., "Nuclear transplantation in early pig embryos," Biol. Reprod., 41:414-8 (Sep. 1989).
Ramirez et al., "Life-supporting human complement regulator decay accelerating factor transgenic pig liver xenograft maintains the metabolic function and coagulation in the nonhuman primate for up to 8 days," Transplantation, 70(7):989-98 (Oct. 15, 2000).
Ramirez-Solis et al., "Gene targeting in embryonic stem cells," Methods Enzymol., 225:855-78 (1993).
Schwarzberg et al., "Germ-line transmission of a c-abl mutation produced by targeted gene disruption in ES cells," Science, 246:799-803 (Nov. 10, 1989).
Starzl et al., "Baboon-to-human liver transplantation," Lancet, 341(8837):65-71 (Jan. 9, 1993).
Starzl et al., "Renal heterotransplantation from baboon to man: Experience with 6 cases," Transplantation, 2(6):752-776 (Nov. 1964).
Starzl et al., "The biological basis of and strategies for clinical xenotransplantation," Immunol Rev., 141:213-244 (Oct. 1994).
Starzl and Putnam, Chapter 19: "Orthotopic Heterotransplantation," Chapter 20: "Pathology of the Orthotopic Homograft and Hetergraft," in Experience in Hepatic TransplantationWB Saunders Company, Philadelphia, PA, pp. 408-471 (1969).
Tuso et al., "Immunochemical characterization of the binding of human immunoglobulins to pig vascular endothelium," Transplant Proc., 24(2):596-7 (Apr. 1992).
Tuso et al., "Pig aortic endothelial cell antigens recognized by human IgM natural antibodies," Transplantation, 56(3):651-5 (Sep. 1993).
Yamada et al., "Marked prolongation of porcine renal xenograft survival in baboons through the use of alpha1,3-galactosyltransferase gene-knockout donors and the cotransplantation of vascularized thymic tissue," Nat. Med., 11:32-34 (Jan. 2005).
Yong and Sykes, "Xenotransplantation: current status and a perspective on the future," Nat Rev Immunol., 7(7):519-31 (Jul. 2007).

* cited by examiner

MINIATURE SWINE TRANSGENIC FOR ONE OR MORE COAGULATION FACTORS

CLAIM OF PRIORITY

This application is a U.S. National Phase Application under 35 U.S.C. § 371 of International Patent Application No. PCT/US2013/045108, filed on Jun. 11 2013, which claims the benefit of U.S. Provisional Application Ser. No. 61/658,674, filed on Jun. 12, 2012, and 61/672,049, filed on Jul. 16, 2012. The entire contents of the foregoing are incorporated herein by reference.

TECHNICAL FIELD

Described are transgenic pigs that express human coagulation factors, as well as cells, tissues and organs from the pigs, and methods of using the same in transplantation procedures, e.g., liver transplants.

BACKGROUND

Every year many patients suffering from end-stage liver disease die of liver failure before they can receive a liver transplant because of the ongoing shortage of donor organs. This shortage is projected to worsen. Alternatives for donor organs (e.g., pig livers) would enable patients with end-stage liver failure to live longer lives.

However, previous attempts have not resulted in long-term viable transplants. Giles et al. (Transplant Proc, 1970, 2(4): p. 506-12) described the first concordant liver xenotransplant procedures, of chimpanzee livers in to children with bilary atresia; the recipients survived only hours post-operatively. Starzl et al. described further attempts using baboon livers, and modern immunosuppression regimes. 1 recipient lived 70 days, 1 died after surgery (Starzl et al., Lancet, 1993. 341(8837): p. 65-71). However, baboon livers are not ideal for a number of reasons.

First transplant attempts using pig livers demonstrated hyperacute rejection of wild type porcine livers, (Makowka et al. (Transplantation, 1995, 59(12): p. 1654-9) described a heterotopic pig to human liver transplant; the recipient experienced hyperacute rejection, and died 34 hours later. Up to 3 days survival was achieved with absorption of anti GalT antibodies (Powelson et al., Transplant Proc. 1994. 26(3): p. 1353-4). Using hDAF transgenic porcine livers, 2 Baboons survived under ICU conditions for 4/8 days; the pig liver produced Coagulation factors, delaying thrombocytopenia (4-5 days) (Ramirez et al., Transplantation, 2000. 70(7): p. 989-98). 4-7 days of survival was found in baboons with 2xGalKO/8xGalKO+CD46tg porcine xeno liver transplants: there was no hyperacute rejection, but fatal, diffuse hemorrhages were seen that were interpreted as a consequence of rapid and persistent thrombocytopenia. Eight animals were euthanized, and three died POD 6-7 (Ekser et al., Am. J. Transplant. 10: 273-285, 2010).

SUMMARY

The present invention is based, at least in part, on the discovery that a species incompatibility in one or more coagulation factors may be the basis of coagulopathy that adversely affects pig-to-primate liver transplants. Thus, described herein are methods of making transgenic pigs that express human coagulation factors, and optionally lack expression of porcine coagulation factors. For example, provided are transgenic swine that express human coagulation factors, human coagulation factor VII, and/or one or more of human coagulation factors II, X and XII and do not express the corresponding porcine coagulation factor or factors, as well as cells, tissues and organs derived therefrom, and their use in transplantation procedures.

Thus, in one aspect, the invention provides transgenic swine in which a human coagulation factor is expressed in at least one organ or tissue type. In some embodiments, the human coagulation factor is selected from the group consisting of human coagulation factor VII, II, X and XII. In some embodiments, the human coagulation factor is expressed in the liver of the swine.

In some embodiments, the normal expression of a porcine coagulation factor is prevented in at least one organ or tissue type. In some embodiments, the transgenic swine has been made to produce a nucleic acid sequence that binds to and prevents the translation of mRNA coding for a porcine coagulation factor in said swine.

In some embodiments, the sequence for the porcine coagulation factor has been replaced by a sequence encoding a human coagulation factor.

In some embodiments, the genome of the transgenic swine has been modified to include a construct comprising a DNA encoding a human coagulation factor operably linked to a promoter therefore. In some embodiments, the promoter is a strong non-tissue specific constitutive or regulatable promoter, or a strong tissue specific constitutive or regulatable promoter, e.g., a promoter that drives expression in the liver of the swine.

In some embodiments, the promoter is from the porcine coagulation factor.

In some embodiments, the transgenic swine lacks expression of porcine alpha(1,3)galactosyltransferase.

In some embodiments, the transgenic swine was grown from a porcine oocyte whose pronuclear material has been removed and into which has been introduced a pluripotent porcine embryonic stem cell that contains a DNA encoding a human coagulation factor operably, and optionally lacks a DNA encoding a functional porcine coagulation factor.

In some embodiments, the transgenic swine was grown from a porcine zygote which has been modified by homologous recombination of a human coagulation factor in an isogenic DNA targeting vector, preferably into the corresponding porcine coagulation factor chromosomal locus. In some embodiments, the isogenic DNA targeting vector comprises a selectable marker gene.

In another aspect, the invention provides porcine cells, in vitro, said cells expressing at least one human coagulation factor. In some embodiments, the human coagulation factor is selected from the group consisting of human coagulation factor VII, and/or one or more of human coagulation factors II, X and XII. In some embodiments, the cells are liver cells.

In some embodiments, the transgenic swine described herein are generated using cells, e.g., ES cells or oocytes in which an alpha (1,3)galactosidase gene has been disrupted, e.g., as described in WO1995028412, which is incorporated by reference herein in its entirety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-B show that coagulation factors in naïve swine and baboon and in the recipient of a porcine liver (B274).

FIGS. 4A-D are line graphs showing the results of liver function tests.

DETAILED DESCRIPTION

The availability of alpha1,3-galactosyl transferase knockout (GalT-KO) miniature swine (Kolber-Simonds et al., 2004. Proc. Natl. Acad. Sci. U. S. A 101: 7335-7340) has improved the prospects of using xenografts to solve the critical shortage of donor organs in the field of transplantation. Using these donors, improvement has been demonstrated in survival for both heterotopic heart (Kuwaki et al., 2005. Nat. Med. 11: 29-31) and orthotopic, life-supporting kidney (Yamada et al., 2005, Nat. Med. 11: 32-34) xenografts over previous studies using standard pig donors. Considering the acute need for donor livers, the present inventors have explored the use of these GalT-KO donors for liver transplantation.

Pig-to-baboon liver xenotransplantation was previously performed using the standard miniature swine as donors, with survivals of up to 3 days (Powelson et al., 1994. Transplant Proc 26: 1353-1354). The first liver xenotransplants using GalT-KO donors survived 6, 9, and 8 days, respectively, and showed no evidence of rejection at the time of death (Kim et al., 2012. Xenotransplantation 19:256-64). Notably, nine days is the longest reported pig-to-primate liver xenograft survival to date.

The cause of death for these animals in all three cases was coagulopathy, characterized by persistent internal bleeding starting a few days after transplantation. Understanding the cause of this coagulopathy is crucial to achieve truly longer survival. While early platelet loss accounts for part of this problem, this thrombocytopenia can be avoided by use of the plasminogen inhibitor aminocaproic acid (Amicar) post-operatively (Kim et al., 2012. Xenotransplantation 19:256-64). However, although the pig liver is clearly able to make coagulation factors (Powelson et al., 1994. Transplant Proc 26: 1353-1354), and at least some of the coagulation factors (including Factor VII) are highly homologous (Chen et al., Blood Cells Mol Dis, 2009 July-August) there appears to be a species incompatibility in one or more of these factors, which we believe may be the basis of the coagulopathy, even after correction of thrombocytopenia. The recipients maintained normal mental status up until their demise, providing compelling evidence of otherwise satisfactory xenograft function. Moreover, the livers showed no signs of immunological rejection at the time of death.

Further evidence that the problem is likely due to insufficient function of one or more coagulation factors rather than loss of platelets was obtained from a heterotopic auxiliary transplant model, in which the native liver was expected to provide primate-specific factors and thereby avoid the coagulopathy. This recipient baboon showed no signs of bleeding for the first nine days following transplantation and survived for 15 days, dying from an infectious complication, again without evidence of rejection.

Thus the present invention provides transgenic swine that express human coagulation factors, e.g., human coagulation factor VII, and/or one or more of human coagulation factors X and XII, and optionally do not express the corresponding porcine coagulation factor or factors.

Thus provided herein are genetically altered animals, more specifically transgenic, chimeric or mosaic swine in which the expression of porcine coagulation factors is prevented, and human coagulation factors are expressed, in at least one organ, tissue or cell type, e.g., in the liver. Transgenic animals carry a gene which has been introduced into the germline of the animal, or an ancestor of the animal, at an early developmental stage. The genetic alteration transgenic animals is stably incorporated into the genome as a result of intentional experimental intervention. Typically, this results from the addition of exogenous foreign DNA or novel constructs (Palmiter et al. 1986. Ann. Rev. Genet. 20:465). With the advent of embryonic stem (ES) cells and specific gene targeting, the definition of transgenesis now includes specific modification of endogenous gene sequences by direct experimental manipulation and by stable incorporation of DNA that codes for effector molecules that modulate the expression of endogenous genes (Gossler et al.

1986. Proc. Natl. Acad. Sci. USA. 83:9065; Schwarzberg et al. 1989. Science 246:799; Joyner et al. 1989. Nature 338:153).

Transgenic Swine

A number of transgenic swine herds have been established that have reduced immunogenicity, and thus reduced likelihood of rejection, for use as cell, organ, or tissue donors in xenotransplantation protocols, and these animals are ideal for use in the present methods. For example, antibodies that bind to alpha-1,3-galactosyltransferase (alpha-1,3-GalT encoded by GGTA1) initiate a rapid graft rejection process known as hyperacute rejection (Yang and Sykes, 2007); this can be avoided by using genetically modified donor pigs that lack functional GGTA1 expression (see, e.g., Yamada et al., Nat. Med. 2005; 11: 32-34; Ozato et al., Transplantation 1982; 34: 113-120; Mezrich et al., Transplantation 2003; 75: 904-907; Kolber-Simonds et al., Proc. Natl. Acad. Sci. U.S.A 2004; 101: 7335-7340). Alternatively or in addition, animals can be used that express human complement regulatory proteins such as CD46, CD55, CD59, or some combination thereof. Transgenes that confer human glycosylation can also be used, e.g., alpha-1,2-fucosyltransferase (alpha-1,2-FT) or human beta-1,4-N-acetylglucosaminyl-transferase III (GnT-III). Transgenic pigs expressing the human complement regulator human complement regulator decay accelerating factor (h-DAF) (Ramirez et al., Transplantation, 2000. 70(7): p. 989-98) can also be used. Multi-transgenic pigs that harbor various combinations of these modifications can also be used. Transgenic strategies that can be used to overcome acute vascular rejection include the expression of human genes for CD39 (ecto-ADPase), endothelial protein C receptor (EPCR), heme oxygenase 1, thrombomodulin, and tissue factor pathway inhibitor (TFPI). Transgenes that overcome cell-mediated rejection can also be included. For a review, see Klymiuk et al., Molecular Reproduction & Development 77:209-221 (2010).

See, e.g., PG Pub No US2013/0111614 (transgenic pigs expressing reduced or no endogenous Sda SDa-like glycans derived from the porcine beta1,4 N-acetyl-galactosaminyl transferase 2 (B4GALNT2) glycosyltransferase and/or reduced or no endogenous alpha-Gal antigens); US2003/0014770 (Transgenic swine in which the normal expression of alpha(1,3) galactosyltransferase is prevented in at least one organ of tissue type); 2007/0033668 (a swine which is homozygous for a major histocompatibility complex haplotype and at least 60% homozygous at all other genetic loci); U.S. Pat. No. 7,141,716 (Inbred miniature swine and uses thereof); U.S. Pat. No. 6,558,663 (Transgenic swine & swine cells having human HLA genes); U.S. Pat. No. 6,469,229 (Inbred miniature swine and uses thereof); U.S. Pat. No. 6,413,769 (alpha(1,3)galactosyltransferase negative porcine cells); U.S. Pat. No. 6,306,651 (Specific tolerance in transplantation); U.S. Pat. No. 6,153,428 (alpha(1,3) galactosyltransferase negative porcine cells); U.S. Pat. No. 6,030,833 (Transgenic swine and swine cells having human HLA genes); U.S. Pat. No. 5,843,425 (Transplantation and graft-versus-host-disease); U.S. Pat. No. 5,614,187 (Specific tolerance in transplantation). Any of these swine can be used in the present methods, as well as wild-type swine, preferably partially inbred miniature swine.

Methods of Generation of Transgenic Coagulation Factor Swine

A number of methods are known in the art for generating the transgenic swine as described herein. One preferred approach for generating a transgenic animal involves microinjection of naked DNA into a cell, preferentially into a pronucleus of an animal at an early embryonic stage (usually the zygote/one-cell stage). DNA injected as described integrates into the native genetic material of the embryo, and will faithfully be replicated together with the chromosomal DNA of the host organism. This allows the transgene to be passed to all cells of the developing organism including the germ line. Transgene DNA that is transmitted to the germ line gives rise to transgenic offspring. If transmitted in a Mendelian fashion, half of the offspring will be transgenic. All transgenic animals derived from one founder animal are referred to as a transgenic line. If the injected transgene DNA integrates into chromosomal DNA at a stage later than the one cell embryo not all cells of the organism will be transgenic, and the animal is referred to as being genetically mosaic. Genetically mosaic animals can be either germ line transmitters or non-transmitters. The general approach of microinjection of heterologous DNA constructs into early embryonic cells is usually restricted to the generation of dominant effects, i.e., one allele of the transgene (hemizygous) causes expression of a phenotype (Palmiter et al. 1986. Ann. Rev. Genetics 20:465.)

In another preferred approach, animals are genetically altered by embryonic stem (ES) cell-mediated transgenesis (Gossler et al. 1986, Proc. Natl. Acad. Sci. USA. 83:9065). ES cell lines are derived from early embryos, either from the inner cell mass (ICM) of a blastocyst (an embryo at a relatively early stage of development) or migrating primordial germ cells (PGC) in the embryonic gonads. They have the potential to be cultured in vitro over many passages i.e. are conditionally immortalized), and they are pluripotent, or totipotent (i.e. are capable of differentiating and giving rise to all cell types. ES cells can be introduced into a recipient blastocyst which is transferred to the uterus of a foster mother for development to term. A recipient blastocyst injected with ES cells can develop into a chimeric animal, due to the contributions from the host embryo and the embryonic stem cells. ES cells can be transfected with heterologous gene constructions that may cause either dominant effects, inactivate whole genes or introduce subtle changes including point mutations. Subsequent to clonal selection for defined genetic changes, a small number of ES cells can be reintroduced into recipient embryos (blastocysts or morulae) where they potentially differentiate into all tissues of the animal including the germ line and thus, give rise to stable lines of animals with designed genetic modifications. Totipotent porcine embryonic stem cells can be genetically altered to have a heterozygous (+/−) mutant, preferably null mutant allele, particularly one produced by homologous recombination in such embryonic stem cells. Alternatively, gene targeting events by homologous recombination can be carried out at the same locus in two consecutive rounds yielding clones of cells that result in a homozygous (−/−) mutant, preferably a null mutant (Ramirez-Solis et al, 1993. Methods in Enzymol. 225:855).

In one preferred embodiment of this invention a knock-in DNA sequence that encodes the corresponding human coagulation factor is integrated into the native genetic material of the swine and produces mRNA for the human coagulation factor. In addition, in preferred embodiments a knockout DNA sequence is integrated into the native genetic material of the swine that prevents the translation of the native mRNA encoding a porcine coagulation factor in the transgenic swine. This knockout sequence can be on the same DNA sequence as the knock-in, or another sequence.

The integrated sequences can be delivered to the cells by various means such as electroporation, retroviral transduction or lipofection.

Knock-In Sequences

In some embodiments the genome of the transgenic swine is modified to include a transgene construct comprising a DNA that encodes a human coagulation factor, e.g., human coagulation factor VII, and/or one or more of human coagulation factors II, X and XII. In preferred embodiments, the DNA encodes the full length mRNA, or encodes a sequence encoding the protein sequence for the human coagulation factor. The GenBank Accession numbers for the sequences for the human coagulation factors are given in Table 1.

TABLE 1

Human Coagulation Factors

| Factor | mRNA Sequence | Protein Sequence | Genomic Sequence |
|---|---|---|---|
| Factor VII | NM_000131.4 | NP_000122.1* | NG_009262.1 |
|  | NM_019616.3 | NP_062562.1** |  |
|  | NM_001267554.1 | NP_001254483.1† |  |
| Factor II | NM_000506.3 | NP_000497.1 | NG_008953.1 |
| Factor X | NM_000504.3 | NP_000495.1 | NG_009258.1 |
| Factor XII | NM_000505.3 | NP_000496.2 | NG_007568.1 |

*variant (1) represents the longest transcript and encodes the longest isoform (a).
**variant (2) lacks an exon in the 5' coding region, but maintains the reading frame, compared to variant 1. The encoded isoform (b) is shorter than isoform a.
†variant (3) lacks three consecutive exons in the 5' coding region, but maintains the reading frame, compared to variant 1. The encoded isoform (c) is shorter than isoform a.

A transgene can direct the expression of an encoded human coagulation factor gene product in one or more cell types or tissues of the transgenic animal. For example, the human coagulation factor can be expressed in the liver of the animal.

Intronic sequences and polyadenylation signals can also be included in the transgene to increase the efficiency of expression of the transgene. A tissue-specific regulatory sequence(s) can be operably linked to a transgene of the invention to direct expression of a human coagulation factor to particular cells. A transgenic founder animal can be identified based upon the presence of a human coagulation factor transgene in its genome and/or expression of human coagulation factor mRNA in tissues or cells of the animals. A transgenic founder animal can then be used to breed additional animals carrying the transgene. Moreover, transgenic animals carrying a transgene encoding a human coagulation factor can further be bred to other transgenic animals carrying other transgenes.

In some embodiments of the invention, cells or cell lines from mutant or non-mutant swine are made with at least one human coagulation factor gene knocked in.

Knockout Sequences

In some embodiments the genome of the transgenic swine is modified to include a construct comprising a DNA complementary to that portion of the porcine coagulation factor coding region that will prevent expression of all or part of the biologically active enzyme. As the term is used "integrated antisense sequence" means a non-native nucleic acid sequence integrated into the genetic material of a cell that is transcribed (constitutively or inducibly) to produce an mRNA that is complementary to and capable of binding with an mRNA produced by the genetic material of the cell so as to regulate or inhibit the expression thereof.

The GenBank Accession numbers for the sequences for the porcine coagulation factors are given in Table 2.

TABLE 1

Porcine Coagulation Factors

| Factor | mRNA Sequence | Protein Sequence | Genomic Sequence |
|---|---|---|---|
| Factor VII | NM_001044591.1 | NP_001038056.1 | NC_010453.4 |
| Factor II | NM_001122985.1 | NP_001116457.1 | NC_010444.3 |
| Factor X | NM_001044592.1 | NP_001038057.1 | NC_010453.4 |
| Factor XII | NM_214242.1 | NP_999407.1 | NW_003540477.1 |

In some embodiments, the transgenic swine has a knockout in the porcine coagulation factor corresponding to the human coagulation factor that is knocked in; for example, if the human coagulation factor VII is expressed, the porcine factor VII is knocked out. Alternatively, in some embodiments the endogenous promoter for the porcine coagulation factor is replaced with an inducible promoter that allows for expression of the porcine coagulation factor while the liver is still in the living pig, but upon removal of the liver from the pig and concomitant withdrawal of the inducing factor the endogenous porcine coagulation factor is no longer expressed. In some embodiments the same or another inducible promoter drives and antisense or other construct described herein that suppresses expression of the human coagulation factor while the liver is still in the living pig.

In some embodiments, the transgenic animal can be one in which an endogenous coagulation factor gene has been altered by, e.g., by homologous recombination between the endogenous porcine coagulation factor gene and a (preferably corresponding) exogenous human coagulation factor cDNA sequence introduced into a cell of the animal, e.g., an embryonic cell of the animal, prior to development of the animal.

In some embodiments of the invention, cells or cell lines from mutant or non-mutant swine are made with at least one human coagulation factor gene knocked in and optionally the corresponding porcine coagulation factor inactivated on one or both alleles, e.g., through the use of an integrated antisense sequence that binds to and prevents the translation of the native mRNA encoding the porcine coagulation factor in said cells or cell lines.

In some embodiments, the transgenic swine is made to produce a ribozyme (catalytic RNA) that cleaves the porcine coagulation factor mRNA with specificity. Ribozymes are specific domains of RNA that have enzymatic activity, either acting as an enzyme on other RNA molecules or acting intramolecularly in reactions such as self-splicing or self-cleaving (Long, D. M., and Uhlenbeck, O. C. 1991 FASEB Journal. 7:25-30). Certain ribozymes contain a small structural domain generally of only about 30 nucleotides called a "hammerhead." The hammerhead is a loop of RNA that is flanked by two linear domains that are specific complements to domains on the substrate to be cleaved. The site on the hammerhead ribozyme that effects the cleavage of substrate is the base of the stem loop or hammerhead.

The DNA for the ribozymes is integrated into the genetic material of an animal, tissue or cell and is transcribed (constitutively or inducibly) to produce a ribozyme that is capable of selectively binding with and cleaving the porcine coagulation factor mRNA. As it is a catalytic molecule, each such ribozyme is capable of cleaving multiple substrate molecules.

The catalytic "stem loop" of the ribozyme is flanked by sequences complementary to regions of the porcine coagulation factor mRNA. In a particularly preferred embodiment the transgenic swine is modified to integrate a construct comprising the DNA coding for that portion of catalytic RNA necessary to inactivate the mRNA of the porcine coagulation factor operably linked to a promoter therefor.

In some embodiments, using cultured porcine embryonic stem cells, a disruptive sequence is introduced by gene targeting at the native genomic locus encoding porcine coagulation factor. In some embodiments the disruptive sequence is a null mutation. In some embodiments, the disruptive sequence is insertion of a sequence encoding a human coagulation factor, e.g., the human coagulation factor that corresponds to the disrupted porcine coagulation factor.

Gene targeting by homologous recombination in ES cells is performed using constructs containing extensive sequence homology to the native gene. In some embodiments, specific mutations are introduced at positions in the porcine coagulation factor gene that are critical for generating a biologically active protein (i.e., null mutations). These mutations can be located in regions important for either translation, transcription or those coding for functional domains of the protein. Alternatively, homologous recombination can be used to replace the porcine coagulation factor with a human coagulation factor, e.g., the corresponding human coagulation factor.

Selection for ES clones that have homologously recombined a gene targeting construct can be achieved using methods known in the art, e.g., detection of specific marker genes. A standard procedure is to use a combination of two drug selectable markers including one for positive selection (survival in the presence of drug, if marker is expressed) and one for negative selection (killing in the presence of the drug, if marker is expressed) (Mansour et al., 1988. Nature 336:348). One preferred type of targeting vector includes the neomycin phosphotransferase (neo) gene for positive selection in the drug G418, as well as the Herpes Simplex Virus-thymidine kinase (HSV-tk) gene for selective killing gancyclovir. Drug selection in G418 and gancyclovir, also termed positive negative selection (PNS) (Mansour et al. 1988. Nature 336:348; Tubulewicz et al, 1991. Cell 65:1153) allows for enrichment of ES cell clones that have undergone gene targeting, rather than random integration events. Confirmation of homologous recombination events is performed using Southern analysis.

The design of a porcine coagulation factor gene targeting construct can be made using methods known in the art, e.g., similar to that described in Example 4 of U.S. Pat. No. 6,153,428. The procedure uses a positive selection (survival) based on integration of the neo (neomycin resistance) gene, optionally in inverse orientation to the corresponding endogenous coagulation factor gene locus, in a cassette with a promoter, e.g., a porcine coagulation factor promoter, and with flanking oligonucleotides complementary to two separate regions of the porcine genome, e.g., a coagulation factor gene sequence. It is understood that other positive selectable markers may be used instead of neo. The neo gene is linked with its promoter to be under control thereof. Downstream from the second flanking sequence is the HSV-tk gene which, if integrated into the genome encodes for production of thymidine kinase making the cell susceptible to killing by gancyclovir (negative selection). The integration of the neo gene but not the HSV-tk gene occurs only where integration into the porcine coagulation factor gene has occurred and provides for both positive and negative selection of the cells so transformed.

In another embodiment of the invention, cells or cell lines from non-mutant swine are made with the porcine coagulation factor inactivated on one or both alleles through the use of an integrated ribozyme sequence which binds to and cleaves the native mRNA encoding the porcine coagulation factor in said cells or cell lines. The integrated ribozyme sequence is delivered to the cells by various means such as electroporation, retrovirai transduction or lipofection.

The swine is preferably a porcine coagulation factor negative/human coagulation factor positive swine grown from a porcine oocyte whose pronuclear material has been removed and into which has been introduced a totipotent porcine embryonic stem cell using protocols for nuclear transfer (Prather et al. 1989, Biol. Reprod. 41:414). ES cells used for nuclear transfer are positive for expression of human coagulation factor, and optionally negative for the expression of porcine coagulation factor, or alternatively, totipotent ES cells used for nuclear transfer are mutated in a targeted fashion in at least one allele of the porcine coagulation factor gene.

The swine is preferably expressing at least one human coagulation factor but lacking expression of the corresponding porcine coagulation factor(s) and bred from chimeric animals that were generated from ES cells by blastocyst injection or morula aggregation. ES cells used to generate the preferably null-mutated chimeric animal were mutated at least in one allele of the porcine coagulation factor gene locus, using gene targeting by homologous recombination.

A chimeric swine is preferably constituted by ES cells that include at least one knock-in gene expressing at least one human coagulation factor, and optionally mutated in one allele of a porcine coagulation factor gene, e.g., the porcine coagulation factor corresponding to the knocked-in human coagulation factor. Derived from mutated ES cells are also germ cells, male or female gametes that allow the mutation to be passed to offspring, and allow for breeding of heterozygous mutant sibling pigs to yield animals homozygous mutant at the a porcine coagulation factor locus. Also described is a swine that expresses human coagulation factors and optionally is deficient for a porcine coagulation factor protein (i.e., characterized by expression of human coagulation factor protein and optionally lack of expression of porcine coagulation factor protein), in which a human coagulation factor is expressed and little, if any, functional porcine coagulation factor are produced. Further described are methods of producing transgenic swine and methods of producing tissue from heterozygous swine or homozygous swine of the present invention. The present invention also relates to cell lines, such as swine cell lines, in which one or more porcine coagulation factor genes are inactivated on one or both alleles and use of such cell lines as a source of tissue and cells for transplantation.

Tissues, organs and purified or substantially pure cells obtained-from transgenic swine, more specifically from hemizygous, heterozygous or homozygous mutant animals of the present invention can be used for xenogeneic transplantation into other mammals including humans in which tissues, organs or cells are needed.

Alternatively, recipient blastocysts are injected or morulae are aggregated with totipotent embryonic stem cells yielding chimeric swine containing at least one allele of a human coagulation factor and preferably null-mutated porcine coagulation factor gene produced by homologous recombination. A chimeric swine is preferably constituted by ES cells mutated in one allele of the porcine coagulation factor gene. Derived from the mutated ES cells are also germ cells that allow the mutation to be passed to offspring, and breeding of heterozygous mutant sibling pigs to yield animals that are homozygous mutants for the human and porcine coagulation factors. Also described is a swine that expresses a human coagulation factor and is optionally deficient for a porcine coagulation factor protein (i.e., characterized by essentially no expression of porcine coagulation factor protein) and with little, if any, functional porcine coagulation factor are produced. Further described are methods of producing transgenic swine and methods of producing tissue from heterozygous swine or homozygous swine of the present invention, and use of such tissue for transplantation. The present invention also related to cell lines, such as swine cell lines, that express human coagulation factor and optionally in which a (preferably) corresponding) porcine coagulation factor gene is inactivated on one or both alleles, and use of such cell lines as a source of tissue, organs and cells for transplantation.

Transplant Procedures

The transgenic swine described herein can be used as a source of tissues or organs, e.g., livers, for transplantation into primates, e.g., into humans. Methods for harvesting and transplanting the organs are known in the art and described herein. For example, the methods can include harvesting the organ from a donor animal; and surgically implanting the organ into a recipient. The recipient can be treated with immunosuppressive therapy as is known in the art, and/or can be treated with the plasminogen inhibitor aminocaproic acid (Amicar) post-operatively (Kim et al, 2012) to treat thrombocytopenia.

EXAMPLES

The invention is further described in the following examples, which do not limit the scope of the invention described in the claims.

Example 1. Up to 9-day Survival and Control of Thrombocytopenia Following Alpha1,3-Galactosyl Transferase Knockout Swine Liver Xenotransplantation in Baboons With standard miniature swine donors, survivals of only 3 days have been achieved in primate liver-transplant recipients. The recent production of alpha1,3-galactosyl transferase knockout (GalT-KO) miniature swine (Kolber-Simonds et al., Proc Natl Acad Sci USA. 2004 May 11; 101(19):7335-40) has made it possible to evaluate xenotransplantation of pig organs in clinically relevant pig-to-non-human primate models in the absence of the effects of natural anti-Gal antibodies. This example describes results using GalT-KO liver grafts.

Materials and Methods

The following materials and methods were used in this example.

Animals

Recipient baboons (Papio hamadryus, n=3, male, blood type B) were purchased from Mannheimer Foundation, Homestead, Fla. Xenogeneic organs were obtained from (GalT-KO miniature swine produced in our own swine facility from breeding stock derived by homologous recombination and nuclear transfer, as previously described (Kolber-Simonds et al., Proc Natl Acad Sci USA. 2004 May 11; 101(19):7335-40). The weights of the recipient baboons were in the 8-10 kg range, while the pig donors were 10-15% smaller.

All animals were cared for according to the Principles of Laboratory Animal Care formulated by the National Society for Medical Research and the Guide for the Care and Use of Laboratory Animals (NIH publication No, 86-23, revised 1985). The experimental protocols were approved b r the Massachusetts General Hospital Institutional Animal Care and Use Committee (IACUC No. 2009N000004).

Surgery

Donor Hepatectomy

Pigs were sedated with glycopyrrolate (0.01 mg/kg), xylazine (1 mg/kg) and Telazoi (2 mg/kg), followed by intubation. Under Fluoroethane inhalation anaesthesia, a midline abdominal incision was made and the liver mobilized. The hilum was dissected next, skeletonizing the hepatic artery down to the celiac trunk and also the portal vein to the confluence of splenic vein and superior mesenteric vein. The bile duct was ligated distally and divided. Next the abdominal aorta was cannulated with a 16 Fr. cannula connected to a cysto-tubing system. After cross-clamping the aorta cephalad to the celiac trunk, the liver was flushed with 1 l of cold Lactated Ringer's followed by 1 l of UW solution (Organ Recovery Systems, Chicago, Ill., USA). The liver was then excised and placed into an intestinal bag surrounded by ice-slush until implantation. Back table biopsies were taken for light and electron microscopy; blood vessels were prepared for anastomosis and the gallbladder was removed.

Recipient Procedures

Five days before the transplant procedure, a dual-lumen port-a-cath system was placed under general anaesthesia into the right internal jugular vein. The venous access chamber was placed subcutaneously between the scapulae. The animal was jacket-trained, and a tether (Lomir, Malone, N.Y., USA) was connected to the jacket. On the day of transplantation, the recipient animal was pre-medicated with Atropine (0.01 mg/kg) and Ketamine (10 mg/kg). After intubation and establishment of maintenance anaesthesia under Fluorothane inhalation, a femoral arterial line and a peripheral large-bore i.v. were placed. Via a midline abdominal incision recipient splenectomy was performed, followed by recipient hepatectomy. Previous experience had established that veno-venous bypass was not needed in these primate recipients (Powelson et al., Transplant Proc. 1994 June; 26(3):1353-4). During the implantation of the donor graft, dopamine was infused as needed to maintain a mean arterial pressure of 50 mmHg. The suprahepatic vena caval anastomosis was fabricated first, followed by the portal vein anastomosis. The liver was then flushed with about 50 ml of blood via the undamped portal vein. It exited via the still open infrahepatic vena cava. Following this flush the infrahepatic vena cava was clamped as the suprahepatic vena cava clamp was removed. This allowed completion of the infrahepatic vena cava anastomosis using 5-0 Prolene (Ethilon, Somerville, N.J., USA) as a continuous running suture during ongoing perfusion of the xenograft. At this point, the dopamine could be weaned. The arterial anastomosis was performed using a donor iliac artery jump graft from the recipient's infrarenal aorta to the celiac trunk of the donor graft. The bile duct was reconstructed as a Roux-en-Y hepaticojejunostomy, using 6-0 PDS. One hour after reperfusion, another liver biopsy was obtained for light and electron microscopy. The animals were rewarmed to 36° C. by flushing the abdominal cavity with warm lactated Ringer's solution. Then, the abdomen was closed in layers. Following initial recovery in the operating room, the animals were transported back to their cages. They were provided oral liquids 6 hours after surgery and soft food within 24 h.

Immunosuppression

The immunosuppressive regimen was based upon that previously described for xenogeneic heart and kidney transplants (Kuwaki et al., Nat Med. 2005 January; 11(1):29-31). As we did not observe any signs of rejection in the first recipient, we modified the regimen to make it less toxic and more clinically applicable in the second recipient. The induction therapy was started with three doses of Thymoglobulin on day −3 in all cases, complemented by LoCd2b (rat anti-primate CD2 IgG2b; Immerge BioTherapeutics, Willington, Del., USA) to ensure T-cell depletion in B274. In the second and third animals LoCd2b was replaced by higher doses of Thymoglobulin. All animals received cobra-venom-factor (Quidel Corp., San Diego, Calif., USA) to deplete complement factors (CH50) before surgery to below 5% of baseline levels, but none was given after transplantation. In addition, anti-CD154 (25 mg/kg) was given on days −1, 0 and 5, and Azathioprine (B291 only) on days −1 and 0. Maintenance therapy was started on day −1 with Tacrolimus (target serum levels 10-25 ng/ml) and a tapering schedule of methylprednisolone starting with 10 mg/kg on day 0.

Clinical Monitoring

Daily blood samples were assayed for complete blood count (Hemavet 950 FS Drew Scientific Group; Waterbury, Conn., USA), chemistry (Catalyst Dx; IDEXX, Holliston, Mass., USA) and Tacrolimus serum levels (Architect i1000SR; Abbott diagnostics, Abbott Park, Ill., USA). Clotting studies were performed in the clinical special coagulation laboratory at Massachusetts General Hospital.

Immunologic Assays

Whole blood CD3 counts were obtained by fluorescent activated cell sorter (FACS) analyses. To measure anti-pig antibody levels, baboon blood was centrifuged at 3100 RPM for 10 min and the sera sterilely aliquoted and stored at −20° C. for later testing. 1×106 PBMCs from a GalT-KO pig were incubated with decomplemented baboon sera for 30 min at 4° C. in the dark. Cells were then washed twice with FACS media to remove any unbound antibody and incubated with fluorescein isothiocyanate-conjugated polyclonal rabbit antihuman IgG (F0058; Dako, Carpinteria, Calif., USA) and IgM (Dako F0185) for 30 min at 4° C. in the dark. Cells were finally washed two times and acquired on a FACS calibur with PI gating to exclude dead cells. Mode fluorescence intensity of baboon antibody binding to pig lymphocytes was analysed using WinList mode analysis software (Verity Software House, Topsham, Me., USA).

Clotting Studies 2 ml of citrated blood was drawn from the port-a-cath system and placed on ice. The samples were immediately transported to the clinical special coagulation laboratory, where they were analysed according to protocols used for human blood.

Results

Operative Course

The weights of the donor swine were 10-15% lower than those of the recipient baboons, as it was we found in preliminary attempts (Powelson et al., supra) that the pig liver has a longer intrahepatic vena cava, which led to kinking in the recipient animals unless the donor animal was of slightly smaller size. No attempt was made to remove the anti-non-Gal antibodies that were present prior to transplant.

Post-Operative Course

B274 experienced a 20-min period of hypotension during the anhepatic phase while the vena cava and portal vein were clamped, but was observed to be sitting on the perch within 30 min of return to its cage, drinking water by six hours and eating by the next morning. Deteriorating LFT's and renal function on POD 2 prompted re-exploration. All hepatic vessels were patent, suggesting the hepatic and renal renal dysfunction probably resulted from hypoxia secondary to fluid overload and pulmonary oedema. Following 36-h intubation and forced diuresis with lasix and mannitol, the animal's condition improved. Liver function then deteriorated again on POD 5, concomitant with a fall in the platelet count to 20 000 per μl and below. Platelets (57×109) were administered, estimated to represent approximately one-third of the recipient's total platelet count, but with no apparent salutary effect. The animal expired on POD 6 with diffuse bleeding. Final pathological examination showed the absence of acute cellular rejection in the liver, but pronounced centrilobular necrosis, attributed to the hypoxaemia in the early perioperative phase. C4d staining was negative in all organs.

Figure 1:
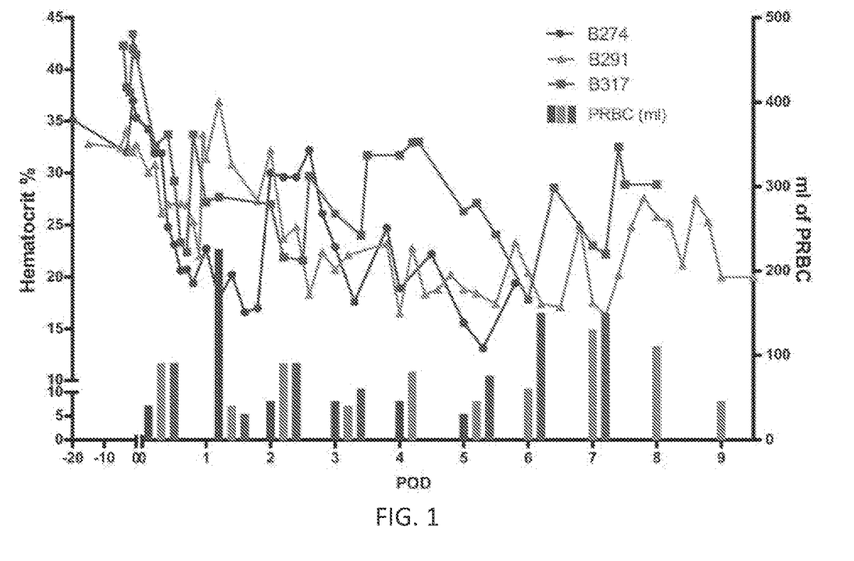
FIG. 1 is a bar graph showing that the hematocrit fell in all animals to critical levels, requiring the transfusion of substantial amounts of packed red blood cells (PRBC). The volume of transfused blood per day is represented by bar graphs.
Figure 2:
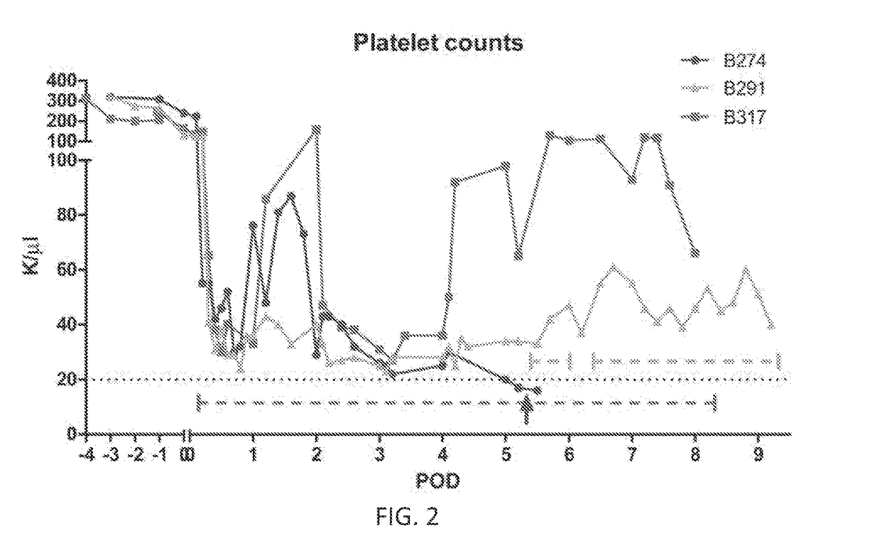
FIG. 2 is a bar graph showing that thrombocytes were lost immediately after reperfusion. However, the levels remained slightly above the critical value of 20 000 per ∥l after Amicar treatment was started. The red and green dotted horizontal lines indicate Amicar infusion in B291 and B317, respectively. The interruption of the green dotted line indicates the accidental discontinuation of Amicar in B291 overnight. The blue arrow marks the time point of transfusion of allogenic platelets in B274 (details see text). B274 did not receive Amicar, while B317 received Amicar throughout its post-operative course.

The second animal (B291) also recovered rapidly, sitting on the perch and eating by the next morning. On POD 2, the animal was explored for a falling hematocrit. Only a small omental bleeding site required coagulation. The volume of blood found in the peritoneal cavity appeared insufficient to explain the low hematocrit (FIG. 1). Over the next 3 days, the platelet count continued to and D-dimer levels were highly elevated. In an attempt to inhibit fibrinolysis, we added Amicar to the therapeutic regimen on POD 5, first as a bolus of 500 mg iv, followed by a continuous infusion of 250 mg/h, similar to the dosing utilized clinically. This intervention was followed by an immediate rise in the platelet count (FIG. 2). When the infusion was inadvertently interrupted for several hours because of a technical problem, the platelet count fell again, but rose following resumption of the infusion. These observations suggested an efficacious effect of the Amicar. The platelet count subsequently remained at >40 000 per with continuous Amicar infusion.

An abdominal culture taken on the second postoperative day became positive for enterococcus within 24 h, probably from peritoneal contamination during construction of the hepaticojejunostomy. This necessitated ongoing antibiotics and further wash-out procedures on POD's 5 and 7. These measures had limited success, as the peritoneal cultures remained positive. These explorations revealed smaller amounts of blood in the peritoneal cavity, now without an identifiable bleeding source. On the final exploration, a large amount of blood was found in the jejunum, ileum and colon. The animal did not recover from this last procedure and died on POD 9. Autopsy revealed clot in small and large intestine, but only superficial erosions of the gastric mucosa. Bilateral pulmonary atelectasis and a 1 cm in diameter recent left ventricle infarction without vascular thrombus were also noted. These findings may have been due to hypotension and depressed respiratory drive in the final hours before the animal's demise. The presumptive cause of death was therapy-refractory sepsis because of intra-abdominal enterococcal infection.

The third animal, B317, received Amicar at the same dose as the 2nd animal, but this time we started the infusion one hour before reperfusion of the graft. The platelet count is again depicted in FIG. 2. This animal also required multiple blood transfusions, similar to the previous two animals (FIG. 1), and surgical explorations were needed on POD 2 and 5. Serosanguinous ascites was found without visible source of bleeding. The animal was active in the first few days, but on POD 2 we detected enterococcus in the ascites culture, and the blood culture grew enterococcus (vancomycin resistant strain). Despite appropriate antibiotics, the animal died on POD 8.

Coagulation Assays

Figure 3A:
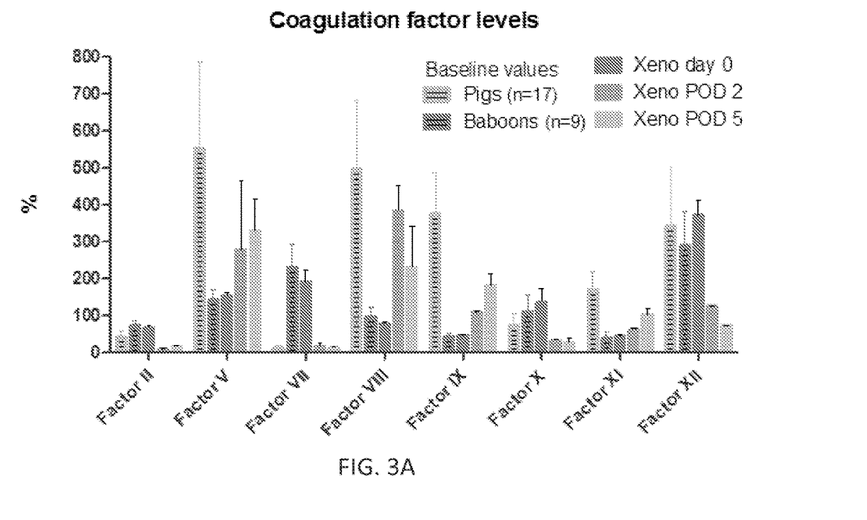
FIG. 3A is a bar graph showing that coagulation factors approached swine baseline levels after transplantation. The Y-axis depicts percent, with 100% being the normal value in humans. The half-lives of the clotting factors ranged from 6 to 12 h, making a transition from baboon to pig highly likely (A).
Figure 3B:
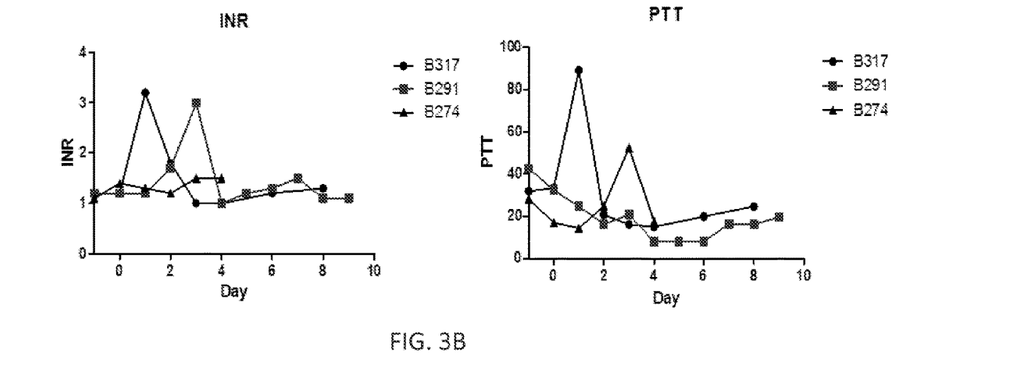
FIG. 3B is a pair of line graphs showing the stable PTT/INR in all three animals with the exception of B274, which experienced post-operative ischaemia and hypoxia.
Figure 4A:
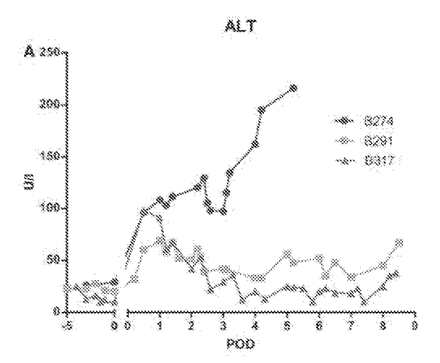
FIG. 4A, Alanine aminotransferase (ALT) levels confirmed stable hepatic function in animal B291 and B317, while B274 exhibited a progressive release of ALT in line with declining liver function, likely due to hypoxia.
Figure 4B:
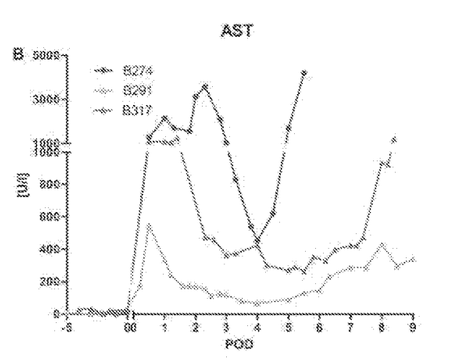
FIG. 4B, aspartate aminotransferase (AST) levels peaked twice after surgery in recipient Baboon 274, and release could be from hepatocytes or haemolyzed red blood cells. AST release appeared less in animals treated with Amicar.
Figure 4C:
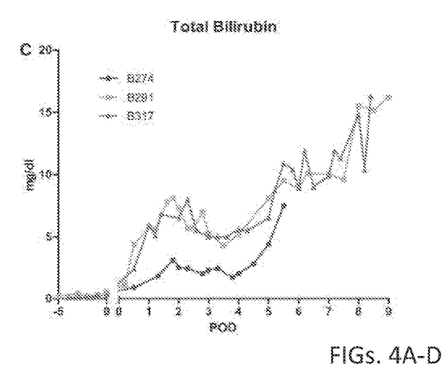
FIG. 4C, Total bilirubin levels rose progressively in all animals. This was likely caused by the continued haemorrhage and haemolysis as the differential analysis showed that it was mostly indirect bilirubin.
Figure 4D:
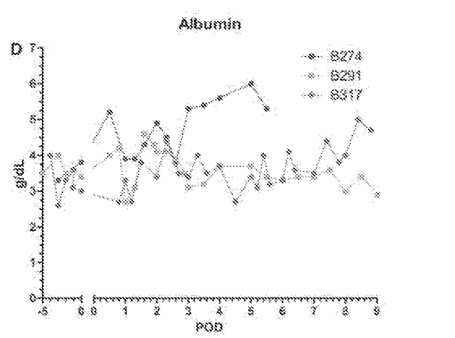
FIG. 4D, Albumin levels remained in normal range throughout the animals' life, but frequent exogenous administration makes interpretation difficult.

Analyses of pig clotting factors following allogenic transplantation or in naïve pigs, revealed inherent differences in baseline values between the pig and baboon (FIG. 3A). Coagulation factors II, VII and X are lower in porcine than in baboon plasma. In contrast, factors V, VIII, IX and XI are noticeably higher in pigs. In general, baboon baseline levels closely resembled the normal range in humans. Some of these measurements were likely influenced by the fact that the assays were designed for human rather than pig plasma, but the levels nevertheless provided a means for assessing the relative contribution of pig vs. baboon factors to the total levels measured. FIG. 3A illustrates a gradual transition in the baboon recipients' baseline levels to porcine levels. These observations confirm the conclusion that the porcine liver resumed normal function in the recipient. Nevertheless, while specific clotting factors were quantitatively sufficient to normalize usual coagulation assays, effective blood clotting was not observed in the abdominal cavity during post-operative explorations. However, PTT and INR remained near normal levels throughout the animals' courses (FIG. 3b).

Post-Transplant Liver Function Tests

The aspartate aminotransferase (AST) in B274 showed an early peak and a 2nd peak on POD 2 before beginning to improve (FIG. 4). After POD4, the AST progressively increased, until the animal's death on POD6. In contrast, in animals B291 and B317, the AST felt after an early peak on POD1 and then never rose to levels seen in B274. Our conclusion was that intraoperative hypotension and reperfusion injury in B274 must have contributed to the early peaks and that the late peak was caused by peri-mortem hypoxia and hypotension. Haemolysis also leads to release of AST, and therefore the data are difficult to interpret. The liver-specific alanine aminotransferase (ALT), in contrast, was increased slightly after surgery in both animals, but returned to almost normal levels in B291 and B317 and did not rise again. Again, in B274, it remained elevated and increased further during the immediate pre-mortem period. The alkaline phosphatase never increased after the transplant procedure to levels higher than preoperative baseline (data not shown). The bilirubin progressively rose after transplantation in all animals (FIG. 4C). As the bilirubin was predominantly indirect, we concluded that haemolysis played a leading role in its generation. The albumin (FIG. 4D) in all animals remained near baseline levels throughout the post-operative course, but large quantities of human albumin were infused daily to treat hypovolaemia.

To maintain the hematocrit above 20%, all animals received an average of 70-80 ml of PRBC's per day (FIG. 1). Amicar administration did not appear to affect this requirement. Bone marrow function was very active, with the reticulocyte count reaching 32% on POD5 in B291, confirming that the drop in hematocrit was not attributable to bone marrow suppression. Other observed abnormal values were the lactate dehydrogenase, which was constantly elevated after transplantation, closely related to the constantly falling hematocrit.

The platelet count in all animals showed a consistent trend, dropping immediately after reperfusion with recipient blood (FIG. 2). A new baseline was then established around 20 000 to 40 000 per µl in animal B274 until POD 5, when the count dropped further. At that point, $57 \times 10^9$ platelets were administered with no salutary effect. The first measurement after the platelet transfusion was actually lower than the pre-infusion value. In B291, a similar drop occurred after reperfusion. But when exploratory laparotomy on POD 5 did not reveal an explanation for the loss of RBC's and platelets in B291, we decided to administer Amicar, which promptly resulted in elevation of platelet counts. B317 received Amicar before reperfusion, and post-operative platelet counts remained 30 000-100 000 per µl throughout the animal's life. In general, animals receiving Amicar never experienced the low platelet count seen in B274.

Histology

Figure 5:
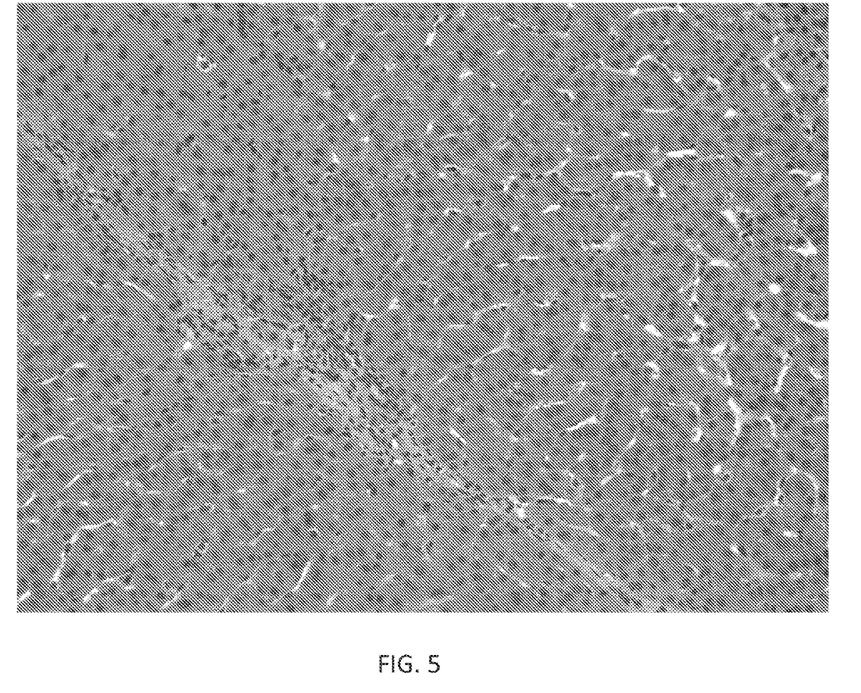
FIG. 5 is a photomicrograph showing normal liver tissue without any evidence of rejection, haematoxylin and eosin. The sample was taken on POD 7, B291. It was representative for all liver samples of all animals in that none of the biopsies ever showed histologic evidence of rejection.

H and E stains of serial liver biopsies did not show any evidence of acute cellular or humoral rejection (FIG. 5 shows the POD 7 histology in B291). In an attempt to define where the platelets and RBC's were degraded, we obtained high-power magnifications of sinusoidal lining cells and hepatocytes. In some areas, iron pigment was found within the hepatocytes, evidence that red blood cells had been degraded. This finding is in concordance with recent observations by Burlak et al., (Xenotransplantation. 2010 September-October; 17(5):350-61) who perfused pig livers ex vivo with human platelets and demonstrated extensive phagocytosis. Electron microscopy revealed occasional platelets within, or closely associated with, liver sinusoidal endothelial cells.

These results suggest for the first time that the loss of platelets may be overcome by administration of aminocaproic acid (Amicar), a plasmin inhibitor, commonly used in cardiac surgery and liver transplantation to treat fibrinolysis. Plasmin, a serine protease, is the key enzyme in the fibrinolytic cascade. It is effectively inhibited by forming a reversible complex with Amicar (Koster and Schirmer, Curr Opin Anaesthesia 2011. February; 24(1):92-7), thereby interrupting the fibrinolytic process. Amicar administration in the treated animals led to stabilization of platelet counts for the longest reported survivals to date of 8 and 9 days. Supporting this conclusion is the observation that temporary interruption of the Amicar infusion led to a drop in platelet count, while restarting the infusion led to stable counts for the following 3 days. Starting the infusion at time of reperfusion led to platelet counts in the 40 000-100 000 per $mm^3$ throughout the animals' life. A remaining difficulty to achieve short-term xenotransplantation survival is the constant need to transfuse RBC's to maintain the recipient's hematocrit. We presume that this requirement was attributable to hemolysis and blood loss despite near normal in vitro clotting parameters and maintenance of platelet counts above 25 000 per $mm^3$. This ongoing blood loss undoubtedly impaired further recovery of the platelet count, and reasons for this persistent coagulopathy required further investigation.

Example 2. Use of Factor Concentrates to Prevent Coagulopathy Following Gal Knockout Pig to Baboon Liver Transplantation As described above in Example 1, we had previously performed pig-to-baboon liver xenotransplantation, using our standard miniature swine as donors, with survivals of up to 3 days (Powelson et al., 1994, Transplant Proc 26: 1353-1354). Our first liver xenotransplants using GalT-KO donors survived 6, 9, and 8 days, respectively, and showed no evidence of rejection at the time of death (Kim et al., 2012. Xenotransplantation 19:256-64). Notably, nine days is the longest reported pig-to-primate liver xenograft survival to date.

The cause of death for these animals in all three cases was coagulopathy, characterized by persistent internal bleeding starting a few days after transplantation. Understanding the cause of this coagulopathy will be crucial to achieve truly longer survival. We and others (Ekser et al., 2010. Am. J. Transplant. 10: 273-285) have found early platelet toss to account for part of this problem, but we have recently found that this thrombocytopenia can be avoided by use of the plasminogen inhibitor aminocaproic acid (Amicar) post-operatively (Kim et al, 2012. Xenotransplantation 19:256-64). However, although the pig liver is clearly able to make coagulation factors (Powelson et al., 1994. Transplant Proc 26: 1353-1354), there appears to be a species incompatibility in one or more of these factors, which we believe may be the basis of the coagulopathy, even after correction of thrombocytopenia. The recipients maintained normal mental status up until their demise, providing compelling evidence of otherwise satisfactory xenograft function. Moreover, the livers showed no signs of immunological rejection at the time of death, Further evidence that the problem is likely due to insufficient function of one or more coagulation factors rather than loss of platelets was obtained from a heterotopic auxiliary transplant model, in which the native liver was expected to provide primate-specific factors and thereby avoid the coagulopathy. This recipient baboon showed no signs of bleeding for the first nine days following transplantation and survived for 15 days, dying from an infectious complication, again without evidence of rejection.

Figure 6:
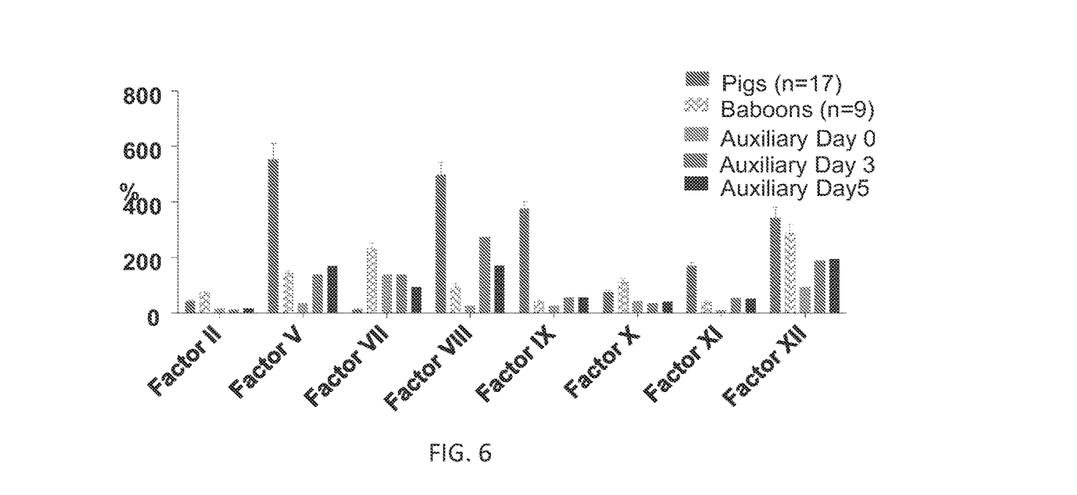
FIG. 6 is a bar graph showing coagulation factors in baboon recipients of auxiliary GalT-KO liver transplants.

A serial study of coagulation factors during the course of our three orthotopic liver xenotransplants (FIG. 3A) has suggested strongly that Factor VII may be the key porcine coagulation that is not functioning properly. These assays are run in a fashion that measures functional coagulation in vitro, using human coagulation components other than the factor being measured. As seen in FIG. 3A, porcine Factor VII is hardly measurable in this assay. In the plasma of post-transplant baboons, Factor VII activity could clearly be measured in this assay on day 0, but was absent by day 2 and thereafter. Further supportive of this finding is the fact that in the animal that received an auxiliary xeno liver (and therefore still had a functioning native liver), the assay measured Factor VII activity (FIG. 6), consistent with the absence of the coagulopathy.

Although levels of coagulation factor VII were the most conspicuous difference in comparing orthotopic transplantation to auxiliary transplantation, levels of coagulation factors II, X and XII were reduced in both experimental models as well. This indicates an element of general coagulation factor consumption. The auxiliary liver recipient had no coagulopathy despite having low levels of these factors, however they may play a role in further exacerbating coagulopathy in the face of factor VII functional deficiency.

Given these findings, we tested the hypothesis that replacement of coaugulation factor VII in the post-operative period after pig-to-baboon liver transplantation will prevent coagulopathy.

The major advantage of Octaplex is that Octaptex contains four coagulation factors (II, VII, IX, X, and proteins C and S) which will allow us to broadly address the coagulation problem we are facing. In the end there might be only one factor be missing/defective, but with the administration of Octaptex we will have a broad base of testing several potential deficiencies in one experiment. An added benefit is that the factors given are not activated, and therefore should not be able to cause hypercoagulabitity.

Subsequently, we performed another pig-to-baboon xenotransplantation. After reperfusion of the xenograft we gave 1 vial of Octaplex (equivalent to 50 IU of factor VII/kg BW). We repeated the dosing every 12 hours. On POD 1 in the afternoon severe swelling of the abdomen developed requiring exploration and ascites drainage. The liver appeared mottled, a liver biopsy showed fibrin deposits. After the procedure the animal did not recover, the ascites recurred within hours and the animal had to be sacrificed. An autopsy was performed which showed fibrin deposits in liver and lungs, all other organs did not show any pathologic changes. It is we likely gave too much factor VII, leading to a hypercoagulable state and subsequent secondary DIC with clotting of the hepatic vasculature.

A further experiment is performed in which a smaller dose is administered, a dose sufficient to prevent DIC and bleeding, but not so much that unwanted thromboses occur.

Example 3. Generation of Coagulation Factor Knockout Swine

In order to provide sufficient human Factor VII activity following xenotransplantation of porcine livers, transgenic swine expressing the human form within the liver are generated. Methods for the stable germline introduction of transgenes into swine are described in the art and include pronuclear injection of DNA into zygotes and transfection of DNA into somatic cells, with the latter serving as nuclear donors in somatic cell nuclear transfer into enucleated oocytes. The coding sequence of the human Factor VII gene is known and, when combined with an appropriate transcriptional promoter, will constitute an expression vector for introduction by either method. Potential promoters are also well described, and without limitation would include promoters for constitutive, ubiquitous expression (e.g., the promoter for human elongation factor 1α) or regulated, tissue specific expression (e.g., the promoter for human Factor VII). In initial experiments, such human transgene sequences would be provided as an addition to the porcine genome, leaving the native porcine Factor VII genes intact.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic swine whose genome comprises a knockout of the endogenous porcine alpha(1,3) galactosyltransferase gene and further comprises a transgene encoding human coagulation factor VII and optionally transgenes selected from the group consisting of human coagulation factor II, X and XII, wherein the human coagulation factor VII, and optionally human coagulation factors II, X or XII are expressed in the liver, the transgenic swine lacks expression of porcine alpha(1,3) galactosyltransferase and does not express an endogenous porcine coagulation factor corresponding to the expressed human coagulation factor selected from the group consisting of porcine coagulation factor VII, II, X and XII.

2. The transgenic swine of claim 1, expresses a nucleic acid sequence that binds to and prevents the translation of mRNA coding for the endogenous porcine coagulation factor.

3. The transgenic swine of claim 1, in which the sequence for the endogenous porcine coagulation factor has been replaced by a sequence encoding the corresponding human coagulation factor.

4. The transgenic swine of claim 1, wherein the transgene encoding human coagulation factor VII and the transgenes selected from the group consisting of human coagulation factor II, X and XII further comprise a promoter operably linked to the sequence encoding the human coagulation factor.

5. The transgenic swine of claim 4, wherein the promoter is a non-tissue specific constitutive or regulatable promoter, or a strong tissue specific constitutive or regulatable promoter.

6. The transgenic swine of claim 4, wherein the promoter is the endogenous porcine coagulation factor promoter.

7. The transgenic swine of claim 1, wherein the swine is produced by a nuclear transfer method comprising:
   a) removing the pronuclear material from a porcine oocyte;
   b) introducing into said oocyte a pluripotent porcine embryonic stem cell that comprises a knockout of the endogenous porcine alpha(1,3) galactosyltransferase gene and further comprises a transgene encoding human coagulation factor VII operably linked to a promoter, and optionally transgenes selected from the group consisting of human coagulation factor II, X and XII, operably linked to a promoter, wherein the oocyte does not express an endogenous porcine coagulation factor corresponding to the expressed human coagulation factor selected from the group consisting of porcine coagulation factor VII, II, X and XII.

8. The transgenic swine of claim 1, wherein the swine is produced by growing a porcine zygote whose genome has been modified by homologous recombination with an isogenic DNA targeting vector comprising the human coagulation factor.

9. The transgenic swine of claim 1, wherein the isogenic DNA targeting vector further comprises a selectable marker gene.

10. The transgenic swine of claim 8, wherein the gene encoding the human coagulation factor is inserted at a porcine coagulation factor chromosomal locus.

11. Porcine cells, in vitro, said cells comprising a knockout of the endogenous porcine alpha(1,3) galactosyltransferase gene and further comprise a transgene encoding human coagulation factor VII, and the cells do not express endogenous porcine Factor VII.

12. The cells of claim 11, wherein the cells further express one or more of human coagulation factors II, X and XII.

13. The cells of claim 11, which are liver cells.

14. The cells of claim 11, which have been modified by homologous recombination of a gene encoding the human coagulation factor VII in an isogenic DNA targeting vector, wherein the gene is inserted into the chromosomal locus of gene encoding the porcine coagulation factor VII.

* * * * *

UNITED STATES PATENT AND TRADEMARK OFFICE
CERTIFICATE OF CORRECTION

PATENT NO. : 9,980,471 B2  
APPLICATION NO. : 14/403764  
DATED : May 29, 2018  
INVENTOR(S) : David H. Sachs et al.

Page 1 of 1

It is certified that error appears in the above-identified patent and that said Letters Patent is hereby corrected as shown below:

In the Claims

In Column 19, Line 3, Claim 5, delete "strong"

Signed and Sealed this
Thirtieth Day of April, 2019

Andrei Iancu
*Director of the United States Patent and Trademark Office*